United States Patent [19]
Gubelmann

[11] Patent Number: 5,958,439
[45] Date of Patent: Sep. 28, 1999

[54] PLANT PROTECTION COMPOSITION CONTAINING ONE OR MORE WATER SOLUBLE ACTIVE MATERIALS AND ONE OR MORE POLYALKOXYLATED AMIDOAMINES

[75] Inventor: Isabelle Gubelmann, Saint Gemain en Laye, France

[73] Assignee: Rhodia Chimie, Courbevoie, France

[21] Appl. No.: 09/011,118

[22] PCT Filed: Aug. 2, 1996

[86] PCT No.: PCT/FR96/01230

§ 371 Date: Jan. 30, 1998

§ 102(e) Date: Jan. 30, 1998

[87] PCT Pub. No.: WO97/05779

PCT Pub. Date: Feb. 20, 1997

[30]  Foreign Application Priority Data

Apr. 8, 1995 [FR] France .................................. 95/09603

[51] Int. Cl.[6] ...................................................... A01N 25/32
[52] U.S. Cl. .......................... 424/406; 424/405; 424/408; 424/409; 424/421; 504/206; 71/DIG. 1; 514/613; 514/617; 514/625; 514/627; 514/629
[58] Field of Search .............................. 504/206; 424/405, 424/406, 408, 409, 421; 514/613, 617, 623–625, 627, 629; 71/DIG. 1

[56]  References Cited

U.S. PATENT DOCUMENTS

| 5,118,444 | 6/1992 | Nguyen | 252/390 |
| 5,663,117 | 9/1997 | Warner | 504/206 |
| 5,668,085 | 9/1997 | Forbes | 504/206 |

OTHER PUBLICATIONS

HCAPlus Abstract of Block Drug Co DE 3005380 Aug. 28, 1980.

Primary Examiner—Neil S. Levy
Attorney, Agent, or Firm—John A. Shedden; Jean-Louis Seugnet

[57]  ABSTRACT

A composition containing, as active ingredient, one or more water soluble plant protection active materials and further containing an effective amount of one or more polyalkoxylated amidoamines of average formula (1) or (2), wherein all $R^1$, which are the same or different, are a straight or branched $C_2$–$C_{22}$ alkyl or alkenyl hydrocarbon group, cycloalkyl or alkylaryl, all $R^2$, which are the same or different, are hydrogen or a $C_1$–$C_4$ alkyl radical, and p, q, r, s and t, which are the same or different, are integers that can be zero, such that p+q is 1–20 and r+s+t is 1–20. Applications of said composition as a herbicide, a fungicide or a fertilizer are also described.

16 Claims, No Drawings

PLANT PROTECTION COMPOSITION CONTAINING ONE OR MORE WATER SOLUBLE ACTIVE MATERIALS AND ONE OR MORE POLYALKOXYLATED AMIDOAMINES

The present invention relates to a plant protection composition including at least one polyalkoxylated amidoamine.

The application of the plant protection active substances to sites to be treated is generally carried out by atomization of corresponding fluid dispersions. These are either solutions in organic solvents, or aqueous dispersions or solutions.

In the case of aqueous solutions, at least one surfactant and/or another compound is generally present with a view to favouring the solubilization and/or increasing the biological activity of the active substance under consideration.

By way of illustration, the conventional aqueous formulations of glyphosate can be mentioned in particular. Glyphosate is a very highly used herbicide of aminophosphate type and its commercial formulations advantageously incorporate an ethoxylated amine.

The presence of this ethoxylated amine considerably increases the biological activity of the glyphosate and in addition leads to a formulation which remains effective whatever the climatic use conditions. In all probability, the ethoxylated amine activates the diffusion of the glyphosate across the cuticular barrier of the plants and/or vegetables.

The interest in these compounds, with synergistic effect on the biological activity, and possibly beneficial effect on the solubility of the active principle with which they are associated, is unfortunately often affected by their chemical toxicity. In fact, the organic solvents, surfactants or subsidiary compounds like the ethoxylated amines pose obvious toxicity problems. The ethoxylated amines thus turn out to be markedly more irritant and toxic than glyphosate itself.

Taking into account, more and more seriously, different problems of ecological nature leads to research into plant protection compositions, preferably water-soluble, endowed with a biological activity comparable to current formulations and on the other hand with markedly reduced toxicity.

The present invention specifically relates to providing a plant protection formulation in keeping with these requirements.

More particularly, the present invention relates to a composition comprising as active principle at least one water-soluble plant protection active substance and additionally comprising an effective quantity of at least one polyalkoxylated amidoamine of average formula (1) or (2):

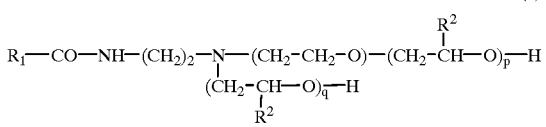

(1)

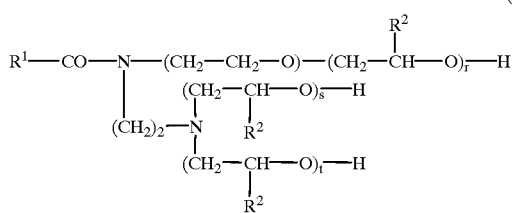

(2)

in which:

$R^1$, which are identical or different, denote a linear or branched alkyl or alkenyl, cycloalkyl or alkylaryl $C_2$–$C_{22}$ hydrocarbon group, $R^2$, which are identical or different, denote hydrogen or a $C_1$–$C_4$ alkyl radical, p, q, r, s and t, which are identical or different, denote integers which can be zero with p+q being between 1 and 20 and r+s+t being between 1 and 20.

Unexpectedly, the abovementioned amidoamines, in the presence of plant protection active substance, have an adequate solubility in aqueous medium and a beneficial effect on the diffusion of this plant protection active substance within cuticular membranes.

Such compounds especially advantageously replace the conventional ethoxylated amines in the plant protection formulations including, for example, as active substance at least one aminophosphate derivative. They lead to formulations with very satisfactory activity and endowed with an appropriate surface tension.

In addition, these compounds have the advantage of being biodegradable and have a very weak irritant character. It is in fact to be noted that these products can especially enter into the composition of cosmetic formulations on account of this property.

Finally, apart from the advantages mentioned above, it has been confirmed that the abovementioned amidoamines also have biological activator properties of plant protection active substances.

However, other advantages and characteristics of the present invention will appear more clearly on reading the description and examples which follow.

Plant protection active substance is understood as meaning, according to the invention, insecticides, herbicides, fungicides but also nutritive elements promoting the growth and development of plants. They are preferably herbicides.

Among the preferred herbicides according to the invention very particular mention will be made of aminophosphate derivatives and preferentially glyphosate, sulphosate, glufosinate and the respective organic or inorganic salts of these compounds. Glyphosate, and preferably its derivatives, are employed.

Glyphosate more particularly means N-phosphonomethylglycine as well as any derivative of this leading in aqueous solution to glyphosate anions.

As derivatives, more particular mention may be made of its alkali metal salts such as sodium or potassium, its substituted or unsubstituted ammonium salts, including secondary or primary amines such as isopropylamine, dimethylamine or diamines such as ethylenediamine, or its sulphonium salts, in particular trimethylsulphonium alone or as a mixture.

With respect to preferred glyphosate derivatives of herbicidal application, the isopropylamine salt and the trimethylsulphonium salt may especially be mentioned.

As far as nutritive elements are concerned, they are preferably metallic salts such as zinc and iron, for example, and preferentially manganese. These salts are used in the form of chelates of EDTA type, for example, or of sulphates.

The compositions according to the invention contain an effective quantity of at least one polyalkoxylated amidoamine of average formula (1) or (2) defined above.

According to a particularly appropriate method of carrying out the invention, the plant protection composition comprises an effective quantity of a mixture of polyalkoxylated amidoamines of average formulae (1) and (2).

According to a preferred variant of the present invention, the radical $R^2$ denotes hydrogen or a methyl radical.

A particular method of carrying out the invention is constituted by polyalkoxylated amidoamines in which the coefficients p, q, r, s and t, which are identical or different, are such that the sum of p and q on the one hand, and the sum of r, s and t on the other hand, are each between 2 and 10.

As polyalkoxylated amidoamines which are particularly suitable, mention may be made of polyethoxylated hydroxyethylcocoylamidoamines containing 3 moles of ethylene oxide, corresponding to formula (1) and/or (2). According to a preferred method of carrying out the invention, such amidoamines are employed as a mixture (formulae (1) and (2)).

These polyalkoxylated amidoamines of formulae (1) and (2) can be prepared, for example, by polycondensation of alkylene oxide with an amidoamine of formula (3) or (4) or a mixture of amidoamines of formulae (3) and (4):

(3)

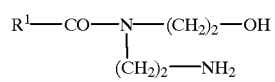
(4)

in which formulae $R^1$ has the definition given above.

This operation can be carried out at a temperature of the order of 70 to 180° C., preferably of the order of 110 to 150° C., by continuous addition of the activated derivative of alkylene glycol in a proportion of the order of 1 to 50 mole equivalents of alkylene oxide with respect to the amidoamines of formula (3) and (4), more particularly of the order of 1.1 to 25 mole equivalents. Preferably, this proportion is of the order of 2 to 20 mole equivalents. Such a procedure is described, for example, in the Patent U.S. Pat. No. 2,681,354.

This operation can additionally be carried out in the presence of a third solvent. By way of example of solvent, it is possible to mention saturated aliphatic hydrocarbons, such as heptane or octane, aromatic hydrocarbons, such as toluene or cumene, ketones such as, especially, octan-2-one, secondary or tertiary alcohols, such as isopropanol or tert-butanol, and water.

The reaction can be carried out in the absence of catalyst, or if necessary in the presence of a catalyst. This catalyst can be acidic, preferably of the Lewis acid type, such as, for example, boron trifluoride, tin tetrachloride or antimony pentachloride. It is likewise possible to employ a basic catalyst especially chosen from the alkali metal hydroxides, such as NaOH or KOH, the alkali metal or alkaline earth metal alkoxides, such as sodium methoxide or potassium tert-butoxide. Suitable catalysts which can likewise be mentioned are rare earth derivatives, such as, especially, the phosphates, carbonates and oxides of lanthanum.

If a catalyst is employed, the quantities employed correspond to approximately 0.05 to 10%, preferably approximately 0.1 to 1%, by weight with respect to the reactive mass.

In the compositions according to the invention, the ratio by weight of the active substance to the amidoamine or to the mixture of amidoamines of formulae (1) and (2) can vary between 1/5 and 10/1.

This ratio is of course adapted according to the use conditions envisaged for the corresponding composition. In any case, it is preferably between 1/2 and 6/1 and preferentially between 2/1 and 4/1.

In the particular case of active substances such as the aminophosphate derivatives, the ratio by weight is understood as active substance expressed in the form of acid equivalent.

The composition is preferably water-soluble.

It can, moreover, be present in the form of an aqueous liquid concentrate intended to be diluted at the time of its use with a view to its atomization. In this type of concentrate, the concentration of active substance(s) can vary between 50 g/l and 500 g/l.

It can likewise be a solid formulation of the granule, powder, lozenge or tablet type. In this case, the polyalkoxylated amidoamine(s) are present therein in a solid form obtained, for example, by adsorption on any appropriate inert support.

Of course, the composition according to the invention can additionally contain other additives. These can be, for example, antifreezing agents such as glycerol or ethylene glycol, colorants, antifoaming agents and/or surfactants.

It can likewise contain an effective quantity of at least one other plant protection active substance. In particular, these can be herbicides chosen from the following products: simazine, isoxaben, atrazine, diuron, terbuthylazine, norflurazon, metamitron, chloridazon and sulphonylurea alone or as a mixture.

The compositions according to the invention, in liquid form or alternatively solubilized in aqueous medium, are compatible on dilution with suspensions and/or concentrated solutions of plant protection active substances of different natures. No flocculation and/or demixing phenomenon in mixtures of the respective solutions is observed.

The present invention likewise relates to the applications of the composition according to the invention as insecticide, herbicide, fungicide or fertilizer.

The composition according to the invention is prepared by simple mixing of the water-soluble plant protection active substance with one or more abovementioned polyalkoxylated amidoamines, possibly in the presence of other additives.

The composition according to the invention can be prepared well before its use but also just before this. In the latter case, the polyalkoxylated amidoamine(s) is/are added to the plant protection active substance, and possibly to the other additives, during the dilution of the formulation in the atomization tank (tank mix).

Some actual examples which do not limit the invention will now be presented.

EXAMPLE 1

A formulation is prepared whose concentration of glyphosate is 360 g/l expressed as acid equivalent, by mixing the following compounds with shaking:

| | |
|---|---|
| * glyphosate isopropylamine salt (46% of acid) | 779 g |
| * amidoamines (*) | 100 g |
| * water | 301 g |

(*) the amidoamines employed correspond to a mixture of polyethoxylated hydroxyethylcocoylamidoamines containing 3 moles of ethylene oxide.

The table below shows that the formulation obtained is stable in the course of time at different storage temperatures:

| STORAGE CONDITIONS | RESULTS |
|---|---|
| initially | 1 clear phase, pH = 5.1 |
| 2 months at 25° C. | 1 clear phase, pH = 5.1 |
| 2 months at 54° C. | 1 clear phase, pH = 5.1 |
| 2 months at 60° C. | 1 clear phase, pH = 5.1 |

In addition, the biological results obtained with the formulation according to the invention, carried out on dicotyledonous plants and on grasses, and especially after 30 days of treatment, are similar to those obtained with formulations containing ethoxylated amines employed in the prior art.

EXAMPLE 2

The following formulation is prepared, containing a concentration of glyphosate of 450 g/l expressed as acid equivalent, by mixing the following compositions with shaking:

| * isopropylamine salt of glyphosate (46% of acid) | 979 g |
| * amidoamines (*) | 100 g |
| * water | 121 g |

(*) the amidoamines employed correspond to a mixture of polyethoxylated hydroxyethylcocoylamidoamines containing 3 moles of ethylene oxide.

The table below shows that the formulation obtained is stable in the course of time at different storage temperatures:

| STORAGE CONDITIONS | RESULTS |
|---|---|
| initially | 1 clear phase, pH = 5.2 |
| 2 months at 25° C. | 1 clear phase, pH = 5.3 |
| 2 months at 54° C. | 1 clear phase, pH = 5.3 |
| 2 months at 60° C. | 1 clear phase, pH = 5.3 |

The biological results obtained with the formulation according to the invention, carried out on dicotyledonous plants and on grasses, and especially after 30 days of treatment, are similar to those obtained with formulations containing ethoxylated amines employed in the prior art.

What is claimed is:

1. A plant protection composition in the form of a liquid concentrate to be diluted at the time of its use comprising between 50 g/l and 500 g/l, as active principle, of one or more water-soluble plant protection active substances and one or more polyalkoxylated amidoamines of average formula (1) or (2):

$$R_1-CO-NH-(CH_2)_2-\underset{\underset{R^2}{|}}{\overset{\underset{|}{(CH_2-CH-O)_q-H}}{N}}-(CH_2-CH_2-O)-(CH_2-\underset{\underset{R^2}{|}}{CH}-O)_p-H \quad (1)$$

$$R^1-CO-\underset{\underset{(CH_2)_2-\underset{\underset{(CH_2-\underset{\underset{R^2}{|}}{CH}-O)_t-H}{|}}{N}-R^2}{|}}{\overset{\underset{|}{(CH_2-\underset{\underset{R^2}{|}}{CH}-O)_s-H}}{N}}-(CH_2-CH_2-O)-(CH_2-\underset{\underset{R^2}{|}}{CH}-O)_r-H \quad (2)$$

wherein:
$R^1$, which are identical or different, denote a linear or branched alkyl or alkenyl, cycloalkyl or alkylaryl $C_2-C_{22}$ hydrocarbon group, $R^2$, which are identical or different, denote hydrogen or a $C_1-C_4$ alkyl radical, and p, q, r, s and t, which are identical or different, denote integers which can be zero with p+q being between 1 and 20 and r+s+t being between 1 and 20, and, wherein the ratio by weight of the plant protection active substane(s), expressed as acid equivalent, to the polyalkoxylated amnidoamine(s) is between 1/5 and 10/1.

2. A composition according to claim 1, comprising an effective quantity of a mixture of polyalkoxylated amidoamines of average formulae (1) and (2).

3. A composition according claim 1, wherein $R^2$ denotes hydrogen or a methyl radical.

4. A composition according to claim 1, wherein the coefficients p, q, r, s and t, are such that p+q is between 2 and 10 and r+s+t is between 2 and 10.

5. A composition according to claim 1, wherein the polyalkoxylated amidoamine(s) is a polyethoxylated hydroxyethylcocoylamidoamine containing 3 moles of ethylene oxide.

6. A composition according to claim 1, wherein the plant protection active substance(s) is an insecticide, a herbicide, a fungicide or a nutritive element promoting the growth and development of plants.

7. A composition according to claim 6, wherein the active substance(s) is a herbicide aminophosphate derivative.

8. A composition according to claim 7, wherein the aminophosphate is glyphosate, sulfosate, glufosinate or one of the respective organic or inorganic salts thereof.

9. A composition according to claim 8, wherein the aminophosphate is glyphosate or the derivatives thereof.

10. A composition according to claim 9, wherein the derivative of glyphosate is an alkali metal salt, a substituted or unsubstituted ammonium salt, a sulphonium salt or a mixture thereof.

11. A composition according to claim 1, wherein the ratio is between 1/2 and 6/1.

12. A composition according to claim 1, further comprising one or more compounds selected from the group consisting of antifreezing agents, colorants, antifoaming agents and surfactants.

13. A composition according to claim 7, further comprising an effective quantity of one or more other active substances selected from the group consisting of simazine, ixobazen, atrazine, diuron, terbuthylazine, norflurazon, metamitron, chloridazon and sulphonylurea.

14. A herbicide comprising a composition as defined in claim 1.

15. A fungicide comprising a composition as defined in claim 1.

16. A fertilizer comprising a composition as defined in claim 1.

* * * * *